United States Patent [19]

Kurz et al.

[11] Patent Number: 4,685,474

[45] Date of Patent: Aug. 11, 1987

[54] DEVICE FOR THE DETERMINATION OF THE INNER DIMENSIONS OF HOLLOW ORGANS

[76] Inventors: Karl H. Kurz, Rheinbabenstr. 5, D-4000 Dusseldorf; Andres Schilling, Fohrenstr. 47, D-7200 Tuttlingen, all of Fed. Rep. of Germany

[21] Appl. No.: 644,070

[22] Filed: Aug. 24, 1984

[30] Foreign Application Priority Data

Aug. 27, 1983 [DE] Fed. Rep. of Germany ....... 3330921

[51] Int. Cl.4 ................................................ A61B 5/10
[52] U.S. Cl. ...................................... 128/778; 33/512
[58] Field of Search ............... 128/778, 775, 774, 737, 128/759, 751; 33/512, 511

[56] References Cited

U.S. PATENT DOCUMENTS

| 3,630,190 | 12/1971 | Baker | 128/778 |
|---|---|---|---|
| 3,738,355 | 6/1973 | Salvatore | 33/512 X |
| 4,016,867 | 4/1977 | King et al. | 33/512 X |
| 4,121,572 | 10/1978 | Krzeminski | 128/778 |
| 4,141,345 | 2/1979 | Allen et al. | 33/512 X |
| 4,204,548 | 5/1980 | Kurz | 128/778 |
| 4,224,951 | 9/1980 | Hasson | 128/778 |
| 4,294,264 | 10/1981 | Fischell et al. | 128/778 |
| 4,362,167 | 12/1982 | Nicolai et al. | 128/778 |
| 4,369,788 | 1/1983 | Goald | 128/751 X |
| 4,489,732 | 12/1984 | Hasson | 128/778 |

FOREIGN PATENT DOCUMENTS

| 0044877 | 2/1982 | European Pat. Off. | 128/778 |
|---|---|---|---|
| 2035097 | 6/1980 | United Kingdom | 128/778 |

Primary Examiner—Henry J. Recla
Assistant Examiner—Angela D. Sykes
Attorney, Agent, or Firm—Leonard Bloom

[57] ABSTRACT

An apparatus for the determination of the inner dimensions of hollow organs, in particular the cavum uteri [uterus cavity], has at its forward end thereof a tube-like probe (10) with two divergable probe tips (32). The probe tips (32) can be spread apart by a translational element which is positioned coaxially within the probe (10). The probe tips (32) are designed as two arms or levers and are attached to two pivots at the forward tip of the probe (10). The translational element is applied behind the pivot points of the probe tips (32). The distance of separation of the probe tips (32) is indicated on a gauge (14).

18 Claims, 12 Drawing Figures

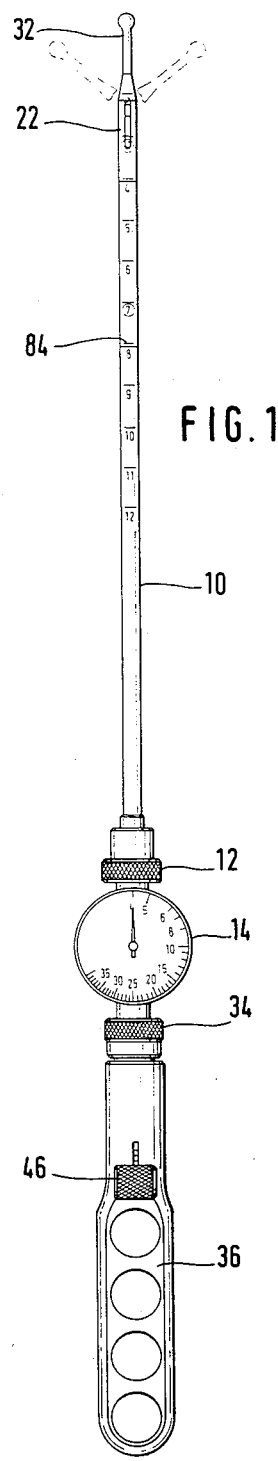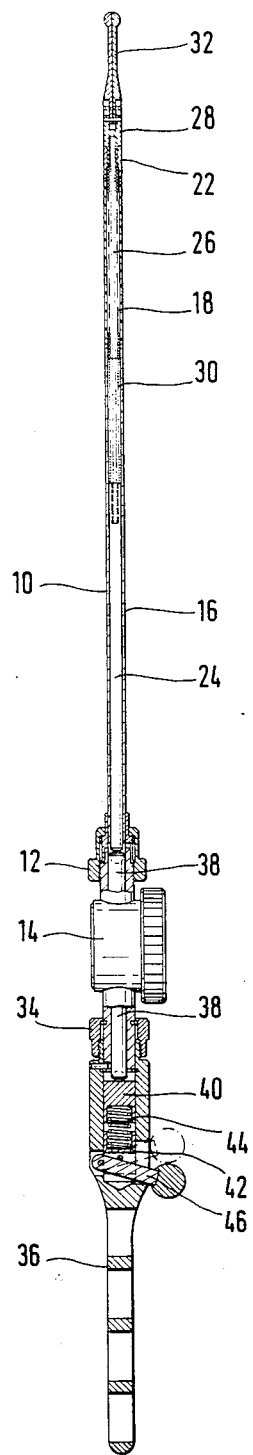

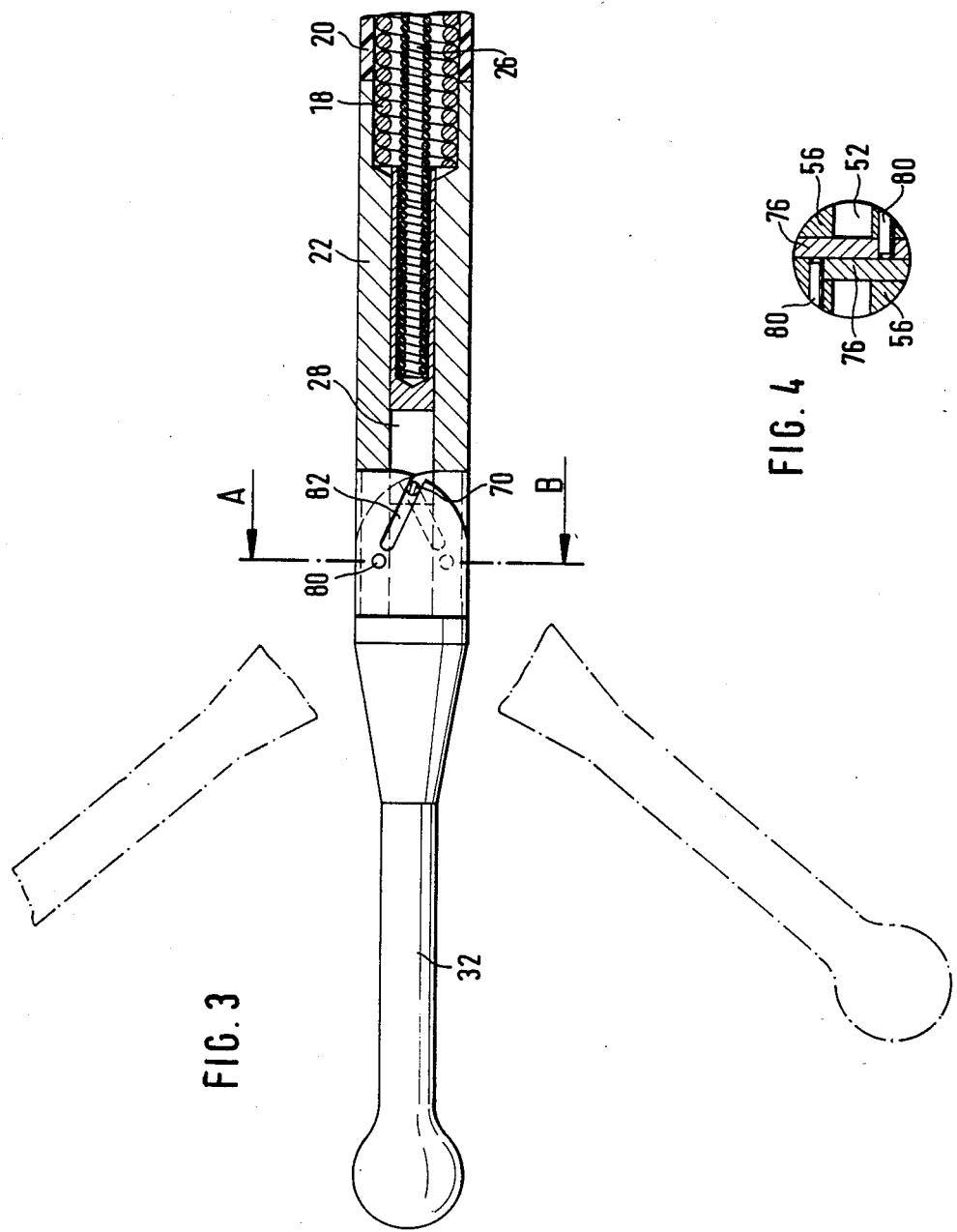

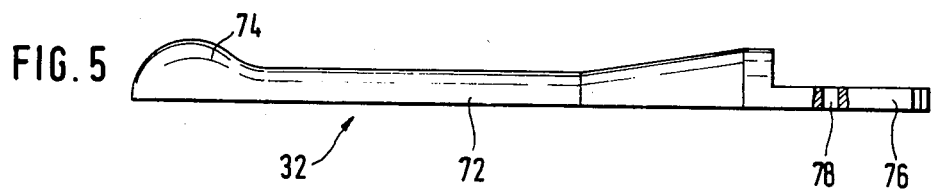
FIG. 5
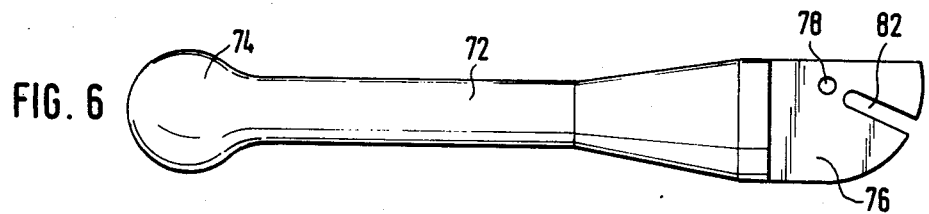
FIG. 6
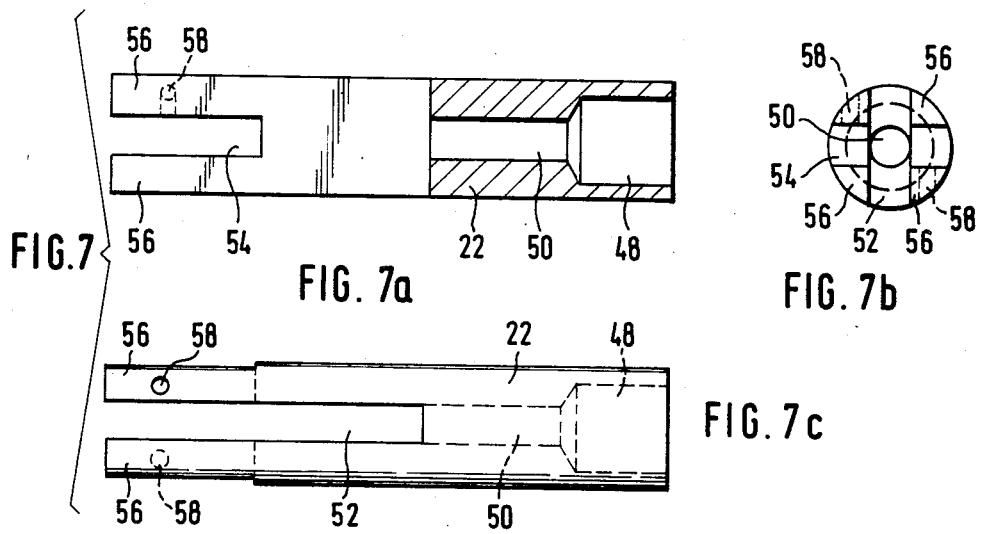
FIG. 7
FIG. 7a
FIG. 7b
FIG. 7c
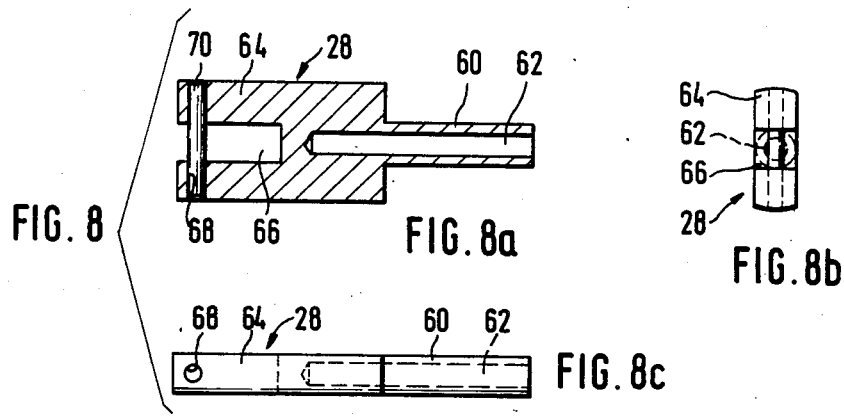
FIG. 8
FIG. 8a
FIG. 8b
FIG. 8c

DEVICE FOR THE DETERMINATION OF THE INNER DIMENSIONS OF HOLLOW ORGANS

FIELD OF THE INVENTION

The present invention relates to a device for the determination of the inner dimensions of hollow organs, and in particular, the cavum uteri.

BACKGROUND OF THE INVENTION

A known device for this purpose consists of a tube-like probe. Attached to the anterior end of the probe are two one-armed lever-fashioned probe tips, which are movable about a common pivot. A rod-like translational element is movable in an axial direction within the probe. The anterior end of the translational element [i.e. the tip]slides past the pivot point of the probe tips in the frontal end of the probe. The anterior end of the translational element is connected to the probe tips via steering levers. The probe tips together with the steering levers form a joint-parallelogram (trapeziem). Accordingly, when the translational element is withdrawn with respect to the probe, the probe tips are spread apart; and when the translational element slides forwardly, the probe tips close.

To measure human or animal hollow organs, the probe is inserted into the hollow organ. The axial depth of penetration serves as an indication of the longitudinal extension of the hollow organ; and through the spreading of the probe tips, the transverse extension of the hollow organ can be explored. At the posterior end of the device there is an indicating device in the form of a similar joint-parallelogram with which a full scale diagram of the explored hollow organ can be made.

The device, which is primarily used for measurements of the cavum uteri of the human reproductive system, must possess relatively-long probe tips due to the joint-parallelogram which is used to spread the probe tips apart. This limits the determination of the transverse extension of cavum uteri, since the probe tips (when spread) will align with the inwardly convexly curved uterus wall. As a result, the head of the probe tip does not reach the uterus wall, especially in the region of the mouth of the fallopian tubes. This can lead to a false measurement.

Furthermore, with the known device the joints of the steering levers must be attached to the probe tips. This constitutes an extraordinary technical difficulty, since the combined cross sectional diameter of the closed probe tips must not exceed a maximum of 4 mm to warrant a safe insertion.

Finally, when the probe tips are fully spread apart, the anterior end of the probe will extend beyond the probe tips and touch the fundic roof of the uterus, such that a complete exploration is prevented.

SUMMARY OF THE INVENTION

The purpose of the present invention is to improve upon, and correct the deficiencies of, the prior art device previously described herein. Accordingly, with a reduced length of the probe tips a complete spreading of the probe tips is possible, and the combined cross sectional diameter of the closed probe tips is at an optimal minimum.

The present invention provides a solution to the problems (inherent in the prior art devices) and provides several advantages as set forth herein.

In the device of the present invention, the probe tips are designed as two arms or levers and are attached to pivots at the forward end of the probe. An axially movable translational element, within the probe, is applied to the probe tips at a point immediately behind the pivot points thereof. As a result, the length of the probe tips (located forwardly of the pivots) is not subject to any limits of construction and, in particular, can be chosen such that a complete separation is possible, without the arms of the probe tips touching the convex contour of the uterus wall. Since the probe does not extend forwardly past the pivot points of the probe tips, the probe tips can be spread apart to extend almost at a right angle from the probe axis, without the forward end of the probe touching the fundic roof of the uterus.

The forward end of the translational element cooperates with guide track (or cam track), which are located rearwardly of the pivot points on the probe tips and are at an angle to the longitudinal axis of the probe. By sliding the forward end of the translational element within those tracks, the probe tips are spread. This is an extremely simple construction, which can be manufactured even under conditions when the physical size is to be kept at a minimum. It is therefore possible to keep the maximum diameter of the probe and the probe tips (in a closed position or mode) small and in particular below the allowable maximum value of 4 mm.

Preferably, both probe tips are not attached to the same pivot, but their pivot points are located opposite to each other on either side of the axial plane of the probe, which bisects perpendicularly the plane of motion of the probe tips. When the probe tips are spread apart, their rearward ends are therefore moved towards the central [longitudinal]axis of the probe; and essentially, these rearward ends of the probe tips remain within the cross sectional area of the probe. In particular, when they are spread apart only a small amount, those rearward ends will not extend past the diameter of the probe. This prevents the rearward ends of the probe tips from damaging the uterus wall tissue, especially in the cervix region.

In the preferred embodiment, a restoring spring is included which pulls back the translational element, such that the probe tips are closed. If the device is not in use, then the probe tips are of necessity in a closed position. The device can thus be inserted without an activation of the probe tips. In particular, an accidental slipping of the hand when the device is in use will not lead to a spreading of the probe tips, but to a closing of the probe tips, thereby preventing any danger of injury.

The axial displacement of the translational element occurs through a gauge, which is attached to the rearward end of the probe, such that an exact and easily readable measurement is effected. Through suitable calibration, the gauge can indicate immediately the separation of the probe tip heads, and therefore the inner dimension of the hollow organ.

The axial displacement of the translational element is facilitated by a movable activation lever which is located in a rearwardly-disposed hand grip. Therefore, the device can be operated comfortably with one hand, such that the device is held by the hand grip and the activation lever is swivelled with the thumb. With this arrangement, the lever translation facilitates an especially sensitive exploration.

In between the activation lever and the translational element, i.e. the measuring bolt of the gauge, a pressure limiting spring is located. This pressure limiting spring allows a displacement of the translational element up to a prescribed force or pressure. If the probe tips encounter a resistance, e.g. when they touch the uterus wall, the pressure of the activation lever increases and the pressure limiting spring gives way, such that this increased pressure is not transmitted to the translational element and thus to the probe tips. Therefore, a reliable protection against damage to the uterus wall is guaranteed, should the device be operated improperly.

The probe with the translational element and the probe tips are removably attached to the hand grip, i.e. the gauge, such that the probe and the probe tips can easily be sterilized.

The probe and the translational element are preferably made flexible (at least in their forward portion) such that they can adjust to the respective position of the uterus.

Each probe tip consists suitably of an arm with an enlarged head. The arms have a semicircular cross section, and the heads are hemispherical. In a closed mode, the heads complement each other to form a full sphere, and the arms form a circular cross section. As a result, the device in its closed position can be inserted without incurring problems.

In a closed mode, the probe tips are aligned in the plane of motion. The protruding heads of the probe tips are perpendicular to the plane of motion; and when spread apart, slide with their smoothly curved surfaces along the uterus wall, such that the irritation of the uterus wall is kept to a minimum. On the outer surface of the probe length, graduations can be applied, such that the device can be used with closed probe tips to measure the length of the cavum uteri.

BRIEF DESCRIPTION OF THE DRAWINGS

FIG. 1 is a top view of the device.

FIG. 2 is an axial cross section of the device in a plane perpendicular to FIG. 1.

FIG. 3 is an enlarged view of the anterior end of the device, to a scale of 5:1.

FIG. 4 is a cross section along line A-B of FIG. 3.

FIG. 5 is an enlarged side-view of the probe tips, to a scale of 5:1.

FIG. 6 shows probe tip of FIG. 5 in a top view.

FIGS. 7 a, b, and c thereof show, (to an enlarged scale of 5:1) the bearing of the probe tips and the slider in a top view, a front view and a side view, respectively.

FIGS. 8 a, b, and c thereof show, (to an enlarged scale of 5:1) the slider in axial cross section, a front view, and top view, respectively.

DESCRIPTION OF THE PREFERRED EMBODIMENT

A preferred embodiment of the present invention is shown in FIGS. 1 and 2, drawn to a reduced scale. The device comprises a tube-like probe (10) which, by means of a sleeve nut (12), is removably attached to the male threaded portion of a conventional gauge (14). The probe (10) includes a rearward portion (16), made from a nonpliable metal tube, and further includes a forward portion. This forward portion comprises a flexible shaft in the form of a screw-spring (18) which is coated with a plastic coating (20). Located forwardly on the probe (10), beyond the flexible shaft, is a metallic fork (22) (which is shown separately in FIG. 7 and which will be described later).

A rod-like translational element is disposed coaxially within the probe (10). This translational element includes a rearward portion, contained within the metallic tube (16) of the probe (10), and consisting of a stiff rod (24). Mounted upon the axial forward end surface of the rod (24) is an elastically pliable wire (26). Mounted upon the forward end of the wire (26) is a slider (28) which is carried within the fork (22). The slider (28) is depicted in detail in FIG. 8 and will be described hereinafter. Due to the elastically pliable, but axially stiff wire (26), the translational element can assume the same flexibility as the forward portion of the probe (10). Located coaxially with the probe (10) is a pressure spring (30) which encloses the wire (26). This pressure spring (30) serves as a restoring spring and is supported axially at its rearward end by the forward end surface of the rod (24), while the forward end of the spring (30) is supported by the rearward end surface of the flexible shaft (18). Therefore, the pressure spring (30) holds the translational element [comprising the rod (24), the wire (26) and the slider (28) within the probe (10) in a withdrawn position.

Two probe tips (32), which are located at the forward end of the device, are shown in detail in FIGS. 5 and 6. The probe tips (32) are pivoted in a bearing of the fork (22). All this shall be described in detail hereinafter.

A sleeve nut (34) attaches a hand grip (36) to the rearward male threads on the gauge (14). The forward (axial) end surface of a measuring bolt (38) of the gauge (14) engages the rearward end of the rod (24) which is part of the translational element. A first bolt (40) engages the rearward end of the measuring bolt (38) and slides axially within the hand grip (36). A second bolt (42) is axially slidable within the hand grip (36) and is located axially behind the first bolt (40). A pressure limiting spring (44) is disposed between bolts (40) and (42).

An activation lever (46), oriented essentially perpendicular to the longitudinal axis of the hand grip (36), is carried at one end within the hand grip (36) and behind the second bolt (42), such that it can be moved within a longitudinal slit of the hand grip (36). The activation lever (46) is aligned with the rearward axial end surface of the second bolt (42), such that the bolt (42) can be moved in an axial forward direction by the activation lever (46). The axial forward displacement of the second bolt (42), caused by the forward movement of the activation lever (46), is translated through the pressure limiting spring (44) onto the first bolt (40), from it onto the measuring bolt (38) of the gauge (14), to the translational element (24) and (26), and through the slider (28) onto the probe tips (32). The pressure-limiting spring (44) assures that the activation lever (46) exerts only a limited axial pressure onto the translational element and therefore onto the probe tips (32). If the probe tips (while being spread apart) encounter a resistance, the axial movement of the translational element will be inhibited, and the pressure limiting spring (44) will be compressed if the activation lever (46) continues its forward motion. Therefore, the pressure of the translational element onto the probe tips will not be increased.

The bearing and activation of the probe tips will be described as follows, with reference to FIGS. 3 to 8 (which show parts of the device enlarged to a scale of 5:1).

As shown in FIG. 3, the rearward end of the probe (10) is formed by a fork (22) shown in detail in FIG. 7a. A bore (48) is formed in the rearward end portion of the fork (22); and the flexible shaft or screw-spring (18) is mounted within the bore (48), such that the fork (22) is attached firmly to the probe. Axially forwardly of the bore (48), is a communicating bore (50) of smaller diameter. At the forward end surface of the fork (22), two slits are located perpendicularly to each other. One slit (52) is oriented axially to the bore (50), whereas the second slit (54) is oriented perpendicular to slit (52) and possesses only half the axial length of slit (52). At the forward end of the fork (22), four sector edges (56) are formed by the axial slits (52) and (54). In two diagonal sector edges (56), bores (58) are located, which run perpendicular to the shorter axial slit (54). Each of the two bores approach slit (54) from opposite directions.

A slider (28), shown in detail in FIG. 8, is carried within the fork (22) and is axially slidable therein. The slider (28) has a rearward cylindrical extension (60) which is inserted into the bore (50) of the fork (22). A coaxial bore (62) extends into the slider (28), into which the wire (26) of the translational element is screwed. Therefore, the slider (28) is connected firmly with the translational element. The forward region of the slider (28) is shaped as a flat plate (64) which slides within the slit (52) of the fork (22). The diametric dimension of the plate (64) corresponds to the outer dimension of the fork (22), such that in the region of the slit (52) they both complement each other to form a circular outer circumference.

A central slit 66 is located in the slider (28) transversly of the diametric extension of its plate (64). A diametric bore (68) is formed in the forward portion of the plate (64), and a pin (70) is inserted within the bore (68).

The forward end of the fork (22) is attached to two probe tips (32), one of which is shown in FIGS. 5 and 6. The other probe tip (32) is shaped so as to be symmetric to, or the mirror image of, the one probe tip (32) shown in FIGS. 5 and 6. Each of the probe tips (32) comprises an arm (72) having a semi-circular cross section and provided with a hemispherical head (74). A plate shaped extension (76) is located at the rearward end of each probe tip (32). Both probe tips (32) are arranged with their flat sides facing each other. The parallel aligned plate shaped extensions (76) of the probe tips (32) are inserted into the shorter axial slit (54) of the fork (22).

A pin (80) is inserted into each bore (58) and is received within a bore (78) on the probe tip extensions (76), thereby pivoting the probe tips on the pins (80).

A guide track (82) is formed in each of the plate-shaped extensions (76) of the probe tips (32). Each guide track (82) is disposed at an angle to the longitudinal axis of the probe tip (32), beginning central to the rearward end of the probe tip in a direction towards the off-center [i.e. off-axis]location of the bore (78).

The rearward end of each probe tip has one rounded-off corner positioned oppositely to the bore (78), as shown in FIG. 6

The pin (70) of the slider (28) rests in the guide tracks (82) of both probe tips (32) and is movable within these tracks.

If no force is exerted onto the activation lever (46), the lever is moved into the position shown in FIG. 2 by the restoring spring (30), and the slider (28) is placed in a completely withdrawn position. In such a position, as shown in FIG. 3, the pin (70) of the slider (28) is located at the rearward ends of the guide tracks (82) of the probe tips (32). Since the rearward ends of the guide tracks (82) are positioned centrally with respect to the probe tips, the probe tips (32) are in a closed position in which they point in the axial direction of the probe (10), being also aligned along their flat sides. In that closed position, the probe tips (32) combine to a single tip having a circular cross section and a spherical head. In that position the probe can be inserted into the uterus, for example.

If the activation lever (46) is moved in a forward direction, then the translational element and therefore the slider (28) move forward against the force of the restoring spring (30). The pin (70) of the slider (28) slides within the guide tracks (82) of the probe tips (32) in a forward direction; and the probe tips [due to the oblique direction of the guide tracks (82) and the off-center bearing of the pins (80)]are swung in opposite directions and are spread apart, as is shown by the broken lines in FIGS. 1 and 3. Because of the curvature of the rearward ends of the probe tips (32), the rearward ends of the probe tips (32) will not extend beyond the outer contours of the fork (22) during the movement of the probe tips (32).

The gauge (14) is preferably calibrated in such a way as to immediately indicate the separation of the heads (74) of the probe tips (32).

As shown in FIG. 1, the outer surface of the probe (10) is provided with length rulings or graduations (84), which indicate the distance to the closed probe tips. With closed probe tips (32), therefore, the device can also be used to measure the longitudinal extension of the cavum uteri.

By means of the sleeve nut (12), the probe (10) with the translational element can be separated from the gauge (14) and the hand grip (36), so as to facilitate easy sterilization of these anterior parts of the device.

Obviously, many modifications may be made without departing from the basic spirit of the present invention. Accordingly, with the scope of the appended claims, the invention may be practiced other than specifically disclosed herein.

What is claimed is:

1. A device for the determination of the inner dimensions of a hollow organ being comprised of: a hollow, tube like probe having a forward end and a rearward end; a rod-like translational element having a forward end and a rearward end, said element being slidably disposed in the probe for coaxial movement therein; a biasing means for constantly urging the translational element in a direction towards the rearward end of the probe; a pin disposed on the forward end of the translational element for axial movement therewith; a pair of diverging probe tips, each of said probe tips being pivotably mounted about a pivot point at the forward end of the probe for movement between a first closed position and a second open position in a vertical plane about the longitudinal axis of the probe, each of said probe tips further having a cam track formed therein, rearwardly of the pivot point, each of said cam tracks being oriented at an angle with respect to the longitudinal axis of the probe tips to simultaneously receive the pin therein, whereby movement of the pin in the cam tracks pivot the probe tips between their first and second positions; means for exerting controlled axial pressure on the rearward end of the translational element for overcoming the pressure of the biasing means and moving the translational element in a direction towards the forward end of the probe so that the pin is received in the cam tracks moving the probe tips from their first position into their second closed position; an indicating device being positioned at the rearward end of the probe responding to and visually displaying the axial displacement of the translational element.

2. The improvement of claim 1, wherein the probe tips are attached opposite to each other and to either side of the axial plane of the probe which perpendicularly bisects the plane of movement of the probe tips.

3. The improvement of claim 1, wherein the translational element further comprising: a stiff rod having a rearward end being positioned in contact with the pressure exerting means for movement in response thereto and further having a forward end; an elastically pliable wire having a rearward end mounted on the axial forward end of the stiff rod for movement therewith and further having a forward end; and a slider mounted on the forward end of the pliable wire for movement therewith and wherein the pin is disposed on the slider.

4. the improvement of claim 3, wherein the biasing means comprises a pressure spring being disposed coaxially within the probe enclosing the pliable wire, said pressure spring having a rearward end being supported by the forward end of the stiff rod and further having a forward end secured to the forward end of the probe.

5. The improvement of claim 3, wherein the indicating device comprises a gauge attached at the rearward end of the probe, a measuring bolt being positioned in abutting arrangement contacting the rearward end of the stiff rod.

6. The improvement of claim 5, further wherein the gauge being located between the translational element and the activation lever (46).

7. The improvement of claim 1, further including a grip being positioned at the rearward end of the probe, and further wherein the pressure exerting means includes a movable activation lever located on the grip, the activation lever being positioned perpendicular to the translational element and adapted to be moved axially thereof.

8. The improvement of claim 7, wherein the pressure exerting means further includes a pressure limiting spring being located between the activation lever and the translational element.

9. The improvement of claim 1, wherein the probe and the indication device are detachably connected.

10. The improvement of claim 1, wherein the forward portions of the translational element and the probe are substantially flexible.

11. The improvement of claim 1, wherein each of the probe tips is comprised of an arm having an enlarged head.

12. The improvement of claim 1, wherein each of probe tips is comprised of an arm, said arms being of substantially semi-circular in cross section; wherein in the first closed position, the arms form a circular cross section.

13. The improvement of claim 12, wherein each of the probe tips is further provided with a head positioned forwardly of the pivot point, said head being substantially hemispherical in shape and further wherein in the first closed position, the heads complement each other to form a substantially full sphere.

14. The improvement of claim 13, wherein in the first closed position, the arms and heads of the probe tips, contact each other along their plane of motion.

15. The improvement of claim 1, wherein graduations are located axially along the length of the outer surface of the probe.

16. The device of claim 1, further wherein each of the probe tips are pivotably mounted upon respective pivot points, said pivot points being positioned opposite to each other on either side of the axial plane of the probe, said pivot points being further positioned upon respective pivot axes, such that movement of the probe tips is in a plane perpendicular to that of the pivot axes.

17. In a device for the determination of the inner dimensions of hollow organs, comprising: a hollow tubular probe having a forward end and a rearward end, a pair of diverging probe tips being pivotably mounted at the forward end of the probe, for pivotal movement between a first closed position and a second open position about a pivot point in a plane being substantially parallel to the longitudinal axis of the probe, a rod shaped translational element having a forward end and a rearward end, said element being slidably disposed in the tubular probe for movement in a direction substantially coaxially within the probe, means for securing the forward end of the translational element to the probe tips at a position rearwardly of the pivot point such that coaxial movement of the translational element pivots the probe tips between their first and second positions, an indicating device being positioned on the probe at the rearward end thereof, said indicating device being responsive to the axial movement of the translational element for responding to and visually displaying the axial displacement of the translational element, a hand grip disposed on a rearward portion of the probe, said hand grip having a forward end and a rearward end and further having an open ended chamber formed in the said forward portion thereof, an activation lever movably mounted in juxtaposition to the hand grip for selective movement of the translational element, thereby facilitating a substantially one-handed operation, biasing means to constantly urge the translational element in a rearward direction so as to maintain the probe tips in their closed position when the activation lever is not moved, thereby facilitating an insertion of the device without an activation of the probe tips, a pressure limiting means for exerting controlled axial pressure on the rearward end of the translational element overcoming the pressure of the biasing means to allow movement of the translational element up to a predetermined force, thereby protecting against damage to the walls of the organ in the event of improper use of the device, and a sleeve nut being positioned between the rearward end of the probe and the hand grip for removably detaching at least the probe, thereby facilitating the sterilization thereof.

18. A device for the determination of the inner dimensions of hollow organs, comprising; a hollow tubular probe having a forward end and a rearward end, a pair of diverging probe tips being pivotably mounted about a pivot point at the forward end of the probe for pivotal movement between a first closed position and a second open position about a pivot point in a plane being substantially parallel to the longitudinal axis of the probe, a rod shaped translational element having a forward end and a rearward end being slidably disposed in the probe for movement in a direction substantially coaxially within the probe means for securing the forward end of the translational element to the probe tips at a position rearwardly of the pivot point such that coaxial movement of the translational element pivots the probe tips between their first and second positions, an indicating device being positioned on the probe at the rearward end thereof, said indicating device being responsive to the axial movement of the translational element for responding to and visually displaying the axial displacement of the translational element, wherein each of the probe tips being further comprised of an arm being substantially semi-circular in cross-section and further having a hemispherical head wherein the maximum diameter of the probe tips in their closed position is less than approximately 4 mm.; and wherein, when the probe tips are in their second open position, the respective end portions of the probe tips well remain substantially within the cross-section contour of the probe, thereby preventing the ends of the probe tips opposite of the hemispherical head from damaging the wall tissues of the organ.

* * * * *